United States Patent [19]

Jones et al.

[11] 4,245,130

[45] Jan. 13, 1981

[54] ISOMERIZATION OF ALKYL AROMATICS USING A GALLIUM CONTAINING ALUMINOSILICATE CATALYST

[75] Inventors: John R. Jones, Weybridge; Dennis C. Wood, Sunbury-on-Thames, both of England

[73] Assignee: The British Petroleum Company Limited, London, England

[21] Appl. No.: 31,040

[22] Filed: Apr. 18, 1979

[30] Foreign Application Priority Data

Jun. 2, 1978 [GB] United Kingdom ............... 26296/78

[51] Int. Cl.$^3$ ................................................ C07C 5/22
[52] U.S. Cl. ................................... 585/481; 585/475; 208/111; 208/139
[58] Field of Search ................ 585/481, 475; 208/111, 208/139

[56] References Cited

U.S. PATENT DOCUMENTS

| | | | |
|---|---|---|---|
| 3,449,456 | 6/1969 | Amir et al. | 585/480 |
| 3,970,544 | 7/1976 | Rosinski et al. | 208/111 |
| 4,056,575 | 11/1977 | Gregory et al. | 585/415 |
| 4,059,645 | 11/1977 | Jacobson | 208/139 |

*Primary Examiner*—Veronica O'Keefe
*Attorney, Agent, or Firm*—Brooks, Haidt, Haffner & Delahunty

[57] ABSTRACT

The present invention relates to a process for the hydrocatalytic treatment of hydrocarbon feedstock which is a mixture of alkyl aromatics containing at least one di- or polymethyl benzene and an alkyl benzene selected from ethyl-benzene, methyl ethyl-benzene and propyl-benzene by contacting the mixture at 300° to 500° C., a pressure of 0 to 100 bars gauge and in the presence of hydrogen with a gallium containing aluminosilicate catalyst and recovering the desired product. The aluminosilicate has a silica to alumina ratio of between 10:1 and 100:1 on a molar bases. The xylene products are useful raw materials as such or for making the corresponding dicarboxylic acids.

10 Claims, No Drawings

ISOMERIZATION OF ALKYL AROMATICS USING A GALLIUM CONTAINING ALUMINOSILICATE CATALYST

The present invention relates to the isomerisation of hydrocarbon mixtures containing alkyl aromatics, particularly those containing isomeric mixtures of xylenes.

Alkyl aromatics, containing 8 or 9 carbon atoms are well known petrochemical feedstocks and established processes exist for the separation of mixtures of alkyl aromatics into individual hydrocarbons. If a specific isomer is desired this is separated from its admixture with the unwanted isomers which may then be further isomerised and the isomerised product recycled to the separation unit.

In the case of fractions containing isomeric mixtures of xylenes, the four main constituents and their boiling points are:
Ethylbenzene: 136.2° C.
Para-xylene: 138.3° C.
Meta-xylene: 139.1° C.
Ortho-xylene: 144.4° C.

It is known that the presence of ethyl benzene causes particular problems in separation processes that involve isomerisation of the unwanted isomers and recycle of the isomerised product. To prevent build up of ethylbenzene in the recycle system one or more of three principal methods have hitherto been adopted. These are:

(1) Fractionation of the feedstock—which is expensive because of the closeness of the boiling points of the components, (2) Bleeding off of a portion of the material from the recycle system, which may involve loss of desirable xylenes, and (3) The use of a catalyst and process conditions in the isomerisation stage which may convert at least a part of the ethylbenzene to more readily separable hydrocarbons. Although some of the desired isomers may also be converted and hence lost by this method, the conversion products are themselves valuable and can be recovered.

Similar considerations apply in the case of $C_9$ alkyl aromatics, where methylethyl- and propyl-benzenes are the problem components in the separation of the trimethyl benzene isomers.

The present invention is concerned with a process for the isomerisation of alkyl aromatics containing these monoalkyl benzenes in addition to the di- or polymethyl benzenes which simultaneously converts ethyl-, methylethyl- or propyl-benzenes to more readily separable hydrocarbons.

Accordingly the present invention is a process for the hydrocatalytic treatment of a hydrocarbon feedstock comprising a mixture of alkyl aromatics containing at least one di- or polymethyl benzene and a monoalkyl benzene selected from ethyl-benzene, methylethyl-benzene and propyl-benzene which process comprises contacting said mixture at a temperature of from 300° to 500° C., a pressure of from 0 to 100 bars gauge and in the presence of hydrogen with a catalyst composition comprising an aluminosilicate having a gallium compound deposited thereon and/or an aluminosilicate in which cations have been exchanged with gallium ions, and recovering a product containing isomerised di- or polymethyl benzenes and a reduced content of the alkyl benzene.

The feedstock for the process of the present invention is suitably the products of a catalytic reforming process. These products comprise mainly a mixture of monoalkyl benzenes, e.g. ethyl and propyl benzenes, and isomeric dimethyl benzenes, i.e. xylenes. Feedstocks containing predominantly mixtures of ethyl benzene and isomeric xylenes particularly meta- and/or ortho-xylenes are preferred.

Under the reaction conditions each of the alkyl benzenes, xylenes and polymethyl benzenes undergoes a series of competing reactions which include isomerisation, disproportionation and dealkylation reactions.

Although none of these reactions can be carried out singly to the total exclusion of the others, under the reaction conditions (i) the monoalkyl benzenes mainly undergo isomerisation to form xylenes or polymethyl benzenes and (ii) the xylenes, methylethyl-benzene or polymethyl benzenes isomerise/disproportionate/dealkylate to result principally in a substantially equilibrium mixture of the isomeric ortho-, meta- and para-xylenes at the reaction temperature used. Some of the xylenes however are inevitably lost through dealkylation and disproportionation to benzene and toluene. For ease of reference these competing reactions will hereafter be termed "conversion" reactions.

The preferred temperature is 350°–450° C. Increase of temperature increases the conversion of monoalkyl benzenes but above 450° C. the extent of xylene disproportionation occurring will give an increasing loss of xylenes. The preferred pressure is 10 to 40 bars gauge. Again increasing pressure not only increases ethyl and propyl benzene conversion but also increases the xylene conversion. The space velocity may be in the range 0.1 to 15 v/v/hr, preferably 0.5 to 5 v/v/hr and the hydrogen/hydrocarbon mole ratio from 1:1 to 20:1, preferably 2:1 to 8:1.

The aluminosilicate used in the catalyst compositions of the present invention is suitably a zeolite containing a high silica to alumina ratio and preferably has a molar ratio of silica to alumina of between 10:1 and 100:1, preferably between 20:1 and 70:1.

The gallium in the catalyst composition may be present as gallium oxide and/or as gallium ions if cations in the aluminosilicate support have been exchanged with gallium ions.

The aluminosilicates in which such an exchange with gallium ions may be carried out may be selected from mordenite, zeolite-$\beta$ and zeolites of the general formula $M_{2/n}O.W_2O_3.ySiO_2zH_2O$ wherein M is a cation which is a positively charged ion selected from a metal ion, an organic ion and a proton of valence n, W is either aluminium or mixtures thereof with gallium, y is an integer between 10 and 100 and z is from 0 to 40. The metal ion is preferably an alkali metal or alkaline earth metal ion, preferably sodium or potassium ions. The organic ions may suitably be represented by the formula $R^1R^2R^3R^4N^+$ or by an ion derived from the diamine $R^1R^2N(CH_2)_xNR^3R^4$ or N-R'—pyrrolidine where $R^1R^2R^3$ and $R^4$ may be H, $CH_3$, $C_2H_5$, $C_3H_7$ or $C_4H_9$ and x equals 2, 3, 4, 5 or 6. The zeolites used are suitably of the ZSM variety, for example ZSM-5 and ZSM-8, and these are extensively described in a number of publications including U.S. Pat. No. 3,970,544 (Mobil).

In the case where the cations in the aluminosilicate have been exchanged for gallium ions, the alkali metal or organic cations normally present in the untreated zeolite may be replaced directly by gallium ions. It is however preferable to decationise the zeolite prior to the exchange. With an aluminosilicate containing alkali metal ions decationisation can be achieved by exchanging of the alkali metal cations with ammonium ions followed by heating at e.g. 250°–600° C. to drive off the ammonia, thus reducing the alkali metal content to less than 0.5% wt. The decationised zeolite is sometimes referred to as being in its hydrogen form, it being assumed that the ion balance is maintained by hydrogen ions. An alternative method is treatment with an acid to decationise the zeolite directly. Suitable acids are hydrochloric or sulphuric acids. Acid treatment may not remove the alkali metal cations to the same extent as ammonium exchange but this is not necessarily disadvantageous and it is not difficult to reduce the alkali metal content to below 1% wt. If the acid treatment uses strong acid of from 5–30% wt strength preferably 10–20% wt strength, an additional effect is obtained, in that aluminium is removed from the crystal lattice with a consequent increase in the silica: alumina ratio. For example, the normal silica to alumina ratio of mordenite is 9–11:1 and this can be increased to 14:1 or more. Increase of time, temperature and acid strength increases the aluminium removal and a convenient acid treatment is with 10–20% wt acid under reflux for 2–12 hours.

After either form of decationisation the zeolite is preferably washed to remove excess acid or ammonium exchange solution and is heated to 250°–600° C.

A zeolite containing an organic cation may be simply decationised by heating to 250°–600° C. to produce the hydrogen form.

In the gallium exchange the gallium ion is suitably provided as an aqueous solution of gallium salts such as for instance gallium nitrate, gallium chloride or gallium sulphate. Such catalysts so produced are subsequently dried. For example an aqueous solution of a gallium compound such as gallium nitrate may be placed in contact with the aluminosilicate at ambient or elevated temperature, e.g. by refluxing. The exchanged aluminosilicate is then separated by decantation followed by filtration, washed several times with deionised water and finally dried.

The process of the present invention may also be carried out using catalysts in which gallium is only impregnated on the surface of the aluminosilicate or is incorporated in the intracrystalline zeolite cavities as a gallium compound which gives rise to gallium oxide during activation of the catalyst prior to contact with the hydrocarbon feedstock. An example of a suitable gallium compound is gallium nitrate. Conventional impregnation techniques may be used to produce these catalysts.

The impregnation may be achieved by preparing a solution, suitably an aqueous solution, of a gallium compound such as for example gallium nitrate and adding a conventional aluminosilicate to this aqueous solution with thorough stirring to form a paste. The paste is subsequently dried at an elevated temperature in vacuum.

Where the catalyst composition is prepared by using a compound of gallium which ionises in aqueous solution for example gallium nitrate it is inevitable that some of the gallium ions will be exchanged with the cations in the aluminosilicate even if the preparation was directed to impregnation of the aluminosilicate.

Whichever method of catalyst preparation is used, the amount of gallium present in the catalyst compositions may vary for instance between 0.1 and 10%, preferably between 0.5 and 7% by weight of the total aluminosilicate in the catalyst composition.

The catalyst composition is suitably activated prior to contact with the hydrocarbon feedstock. The activation may be carried out by heating the catalyst at a temperature of between 250° C. and 600° C., preferably between 350° C. and 500° C. Activation may be carried out in an atmosphere of hydrogen, air or a gas inert under the reaction conditions such as nitrogen, but most preferably in an atmosphere of hydrogen.

As indicated above an alkyl aromatic isomerisation process is generally used in conjunction with a recovery process. The isomerised products of the present invention may therefore be recovered by passing the mixture containing di- and polymethyl benzenes and the alkyl benzenes, if necessary after fractionation to remove hydrocarbons of higher and lower carbon number than the isomerisation feedstock to a separation step in which a di- or polymethyl benzene is separated. The mixture thus depleted in said di-or polymethyl benzene is then passed to an isomerisation step.

In a particularly preferred embodiment of the present invention, the catalytic reformate stream used as feedstock may be subjected to a fractional distillation step in which the bulk of the ortho-xylene in the isomeric mixture is removed as a base product. The overhead product from this distillation consists mainly of a mixture of metaxylene, para-xylene and ethyl benzene. This mixture is passed to a para-xylene separation step for a conventional separation by crystallisation or absorption to separate para-xylene therefrom. The mixture remaining after the separation by crystallisation or absorption is rich in meta-xylene and ethyl benzene. This latter mixture is fed into an isomerisation reactor and is isomerised in accordance with the present invention. The isomerised products may be wholly combined with the catalytic reformate stream and recycled to the fractional distillation step, or, a part of the isomerised products may be fed directly to the p-xylene separation step along with the base products of the distillation step. Prior to recycle to the fractional distillation step or to the p-xylene separation step, the isomerised products may be fractionated, if necessary, to remove hydrocarbons of higher and lower carbon numbers than the feedstock to the isomerisation step. The fractionated isomerised products may then be channelled as before. This sequence of steps may be operated continuously.

The invention is illustrated by the following examples.

EXAMPLE 1

5 grams of gallium metal were dissolved in 38 mls concentrated nitric acid. This solution was then diluted to 400 mls by addition of deionised water and an ammonia solution giving a resulting solution with a pH of 3. 100 grams of ZSM-8 were stirred and refluxed with this solution for 48 hours with the pH being adjusted to 3 at intervals by further addition of ammonia solution. After refluxing the solid was filtered and washed thoroughly with deionised water. The resulting gallium exchanged ZSM-8 was then slurried with a silica sol prepared by mixing 59 mls Ludox AS-40 with 41 mls of deionised water. The resulting slurry was dried at 110° C. overnight in a vacuum oven and then granulated to 8–30 mesh. It was calcined at 550° C. for 4 hours and the composition shown in Table 1 was obtained.

15 mls of this catalyst composition was loaded into a quartz reactor and heated at 550° C. for 45 minutes in a stream of hydrogen. A $C_8$ aromatics blend made up to represent a typical mother liquor from a para-xylene separation process with a component analysis as set out in Table 2 was fed to the reactor whilst maintaining the hydrogen stream. The product gases were condensed and a liquid sample was taken between 10 and 20 minutes on stream. The detailed operating conditions and the product analysis are set out in Table 2, and the approach to equilibrium of the xylenes is shown in Table 3.

EXAMPLE 2

5 grams of gallium metal were dissolved in 38 mls concentrated nitric acid. This solution was then diluted to 400 mls by addition of deionised water and an ammonium solution giving a resulting solution with a pH of 3. 100 grams of zeolite beta were stirred and refluxed with this solution for 48 hours with the pH being adjusted to 3 at intervals by small additions of concentrated nitric acid. After refluxing the solid was filtered and washed thoroughly with deionised water. The resulting gallium exchanged zeolite beta was then stirred with a silica gel prepared by mixing 56 mls Ludox AS-40 with 44 mls of deionised water. The resulting slurry was dried at 110° C. overnight in a vacuum oven and then granulated to 8-30 mesh. It was calcined at 550° C. for 4 hours and the composition is shown in Table 1.

15 mls of the catalyst were hydrogen pretreated and tested for xylenes isomerisation as in Example 1. The detailed operating conditions and the product analysis are set out in Table 2, and the approach to equilibrium of the xylenes isomers is shown in Table 3.

EXAMPLE 3

5 grams of gallium metal were dissolved in 38 mls concentrated nitric acid and this solution was diluted to 400 mls by addition of deionised water and an ammonia solution giving a resulting solution with a pH of 3. 117 g of a zeolite omega obtained from Union Carbide in its hydrogen form was stirred and refluxed with this solution for 48 hours, with the pH being adjusted to 3 at intervals by the addition of more ammonia solution. After refluxing the solid was filtered and washed thoroughly with deionised water and dried. The resulting gallium exchanged zeolite omega was then powered and stirred with a silica sol prepared by mixing 60 mls Ludox AS-40 with 40 mls of deionised water. The resulting slurry was dried at 110° C. for 48 hours and then granulated to 8-30 mesh. It was calcined at 550° C. for 4 hours and the composition is shown in Table 1.

15 mls of the catalyst were hydrogen pretreated and tested for xylenes isomerisation as in Example 1. The detailed operating conditions and the product analysis are set out in Table 2, and the approach to equilibrium of the xylenes isomers is shown in Table 3.

EXAMPLE 4

5 grams of gallium metal were dissolved in 38 mls concentrated nitric acid and this solution was diluted to 400 mls by addition of deionised water and an ammonia solution giving a resulting solution with a pH of 3. 90 grams of offretite (Grace) was stirred and refluxed with this solution for 24 hours with the pH being adjusted to 3 at intervals by the addition of drops of concentrated nitric acid. After refluxing the solid was filtered and washed thoroughly with deionised water. The resulting exchanged gallium offretite was stirred with a silica sol prepared by mixing 49 mls Ludox AS-40 with 51 mls deionised water. The resulting slurry was dried in a vacuum oven with temperature increased from 50° C. to 110° C. over 8 hours, and then granulated to 8-30 mesh. It was calcined at 850° C. for 4 hours and the composition is shown in Table 1.

15 mls of the catalyst were hydrogen pretreated and tested for xylenes isomerisation as in Example 1. The detailed operating conditions and the product analysis are set out in Table 2, and the approach to equilibrium of the xylenes isomers is shown in Table 3.

EXAMPLE 5

5 grams of gallium metal were dissolved in 38 mls concentrated nitric acid and this solution was diluted to 400 mls by addition of deionised water and an ammonia solution giving a resulting solution with a pH of 3. 145 grams mordenite in its hydrogen form was stirred and refluxed with this solution for 24 hours with the pH being adjusted to 3 at intervals by the addition of more ammonia solution. After refluxing the solid was filtered and washed thoroughly with deionised water. The resulting exchanged gallium mordenite was dried in a vacuum oven with temperature increased from 45° C. to 110° C. over 8 hours, and then granulated to 8-30 mesh. It was calcined at 550° C. for 4 hours and the composition is shown in Table 1.

15 mls of the catalyst were hydrogen pretreated and tested for xylenes isomerisation as in Example 1. The detailed operating conditions and the product analysis are set out in Table 2, and the approach to equilibrium of the xylenes isomers is shown in Table 3.

EXAMPLE 6

30 grams of the catalyst prepared as in Example 1 were packed into a metal reactor in the following manner.

The reactor was split into four zones of volumes 45, 44, 38 and 73 ml from the reactor top to bottom and the catalyst was packed into these zones mixed with a diluent of 8-16 BSS quartz with volume of catalyst to volume of quartz ratios of 0.1, 0.26, 0.27 and 0.43 respectively. The catalyst was activated by heating to 482° C. in a stream of hydrogen, GHSV 1000, at a pressure of 16.5 bar (g) and held at that temperature for four hours. The reactor was allowed to cool to 400° C. maintaining hydrogen recycle before the feed, a typical mother liquor from a para-xylene separation process with a component analysis as set out in Table 4, was fed to the reactor at a WHSV of 3.0 whilst maintaining the hydrogen stream. The reactor temperature was raised to 427° C. with the hydrogen to hydrocarbon molar ratio being maintained at about 5:1 and a recycle gas rate of 10 moles per hour. The liquid product was collected and the product analyses are set out in Table 4, and the approach to equilibrium of the xylenes is shown in Table 5.

TABLE 1

| Example No | 1 | 2 | 3 | 4 | 5 |
|---|---|---|---|---|---|
| Ga content % wt | 3.95 | 4.69 | 4.50 | 4.78 | 3.98 |
| Al content % wt | 1.0 | 2.6 | 7.0 | 6.8 | 5.6 |
| Si content % wt | 44.0 | 43.0 | 38.0 | 36.0 | 41.0 |
| $SiO_2$: $Al_2O_3$ mole ratio | 85:1 | 32:1 | 11:1 | 10:1 | 14:1 |
| Surface Area $m^2/g$ | 290 | 415 | 110 | 305 | 360 |
| Pore Volume ml/g | 0.20 | 0.34 | 0.18 | 0.25 | 0.18 |

TABLE 2

| Example No | Feedstock | 1 | 2 | 3 | 4 | 5 |
|---|---|---|---|---|---|---|
| Operating Conditions | | | | | | |
| Reactor pressure | — | Atmospheric | Atmospheric | Atmospheric | Atmospheric | Atmospheric |
| Catalyst bed temperature °C. | — | 400 | 400 | 400 | 400 | 400 |
| Liquid space velocity v/v/hr | — | 1.01 | 1.12 | 1.05 | 1.01 | 1.01 |
| $H_2$: Hydrocarbon mole ratio | — | 7.6:1 | 6.6:1 | 6.9:1 | 7.2:1 | 7.3:1 |
| Liquid Product Analyses % wt | | | | | | |
| Benzene | 0.1 | 6.2 | 4.3 | 2.8 | 0.7 | 1.5 |
| Toluene | 0.4 | 3.0 | 25.3 | 13.0 | 3.1 | 12.0 |
| Ethylbenzene | 19.7 | 5.8 | 2.9 | 9.6 | 16.8 | 11.7 |
| para-xylene | 12.3 | 19.4 | 11.0 | 14.4 | 17.0 | 15.8 |
| meta-xylene | 57.9 | 45.4 | 26.3 | 33.2 | 44.7 | 36.0 |
| ortho-xylene | 9.6 | 19.5 | 11.0 | 14.2 | 15.5 | 14.5 |
| $C_9$ Alkyl aromatics | — | 0.7 | 19.2 | 12.8 | 2.2 | 8.5 |
| Total Xylenes % wt | 79.8 | 84.3 | 48.3 | 61.8 | 77.2 | 66.3 |
| Ethylbenzene destroyed % | — | 70.6 | 85.3 | 51.3 | 14.7 | 40.6 |
| Xylenes retained % | — | 105.6 | 60.5 | 77.4 | 96.7 | 83.1 |

TABLE 3

| Example No. | Equilibrium at 400° C. | 1 | 2 | 3 | 4 | 5 |
|---|---|---|---|---|---|---|
| Xylene Distribution % | | | | | | |
| Para- | 23.4 | 23.0 | 22.8 | 23.3 | 22.0 | 23.8 |
| Meta- | 52.3 | 53.9 | 54.4 | 53.7 | 57.9 | 54.3 |
| Ortho- | 24.3 | 23.1 | 22.8 | 23.0 | 20.1 | 21.9 |
| Approach to Equilibrium of each Xylene Isomer % | | | | | | |
| Para- | — | 95.0 | 92.5 | 98.8 | 82.5 | 105.0 |
| Meta- | — | 92.1 | 89.7 | 73.1 | 72.4 | 90.2 |
| Ortho- | — | 90.2 | 87.8 | 89.4 | 65.9 | 80.5 |

TABLE 4

| Hours on stream | Feedstock | 19–43 | 91–115 | 139–163 |
|---|---|---|---|---|
| Operating Conditions | | | | |
| Reactor pressure bar (g) | — | 16.5 | 16.5 | 16.5 |
| Catalyst bed temperature °C. | — | 427 | 427 | 427 |
| WHSV | — | 3.0 | 3.0 | 3.0 |
| $H_2$: hydrocarbon mole ratio | — | 4.4 | 4.8 | 6.3 |
| Liquid product % wt on feed | | | | |
| Paraffins and naphthenes | 5.0 | 12.4 | 6.6 | 5.2 |
| Benzene | trace | 7.3 | 7.0 | 7.1 |
| Toluene | 1.0 | 4.3 | 3.1 | 2.9 |
| Ethylbenzene | 21.9 | 7.7 | 9.9 | 9.9 |
| para-Xylene | 11.0 | 13.6 | 15.4 | 15.3 |
| meta-Xylene | 56.8 | 32.1 | 37.1 | 37.2 |
| ortho-Xylene | 4.3 | 13.6 | 14.3 | 14.3 |
| $C_9$ Alkyl aromatics | 0.0 | 2.1 | 2.0 | 2.0 |
| | 100.0 | 93.1 | 95.4 | 93.9 |
| Total Xylenes % wt | 72.1 | 59.3 | 66.8 | 66.8 |
| Ethylbenzene destroyed % | — | 64.8 | 54.8 | 54.8 |
| Xylenes retained % | — | 82.3 | 92.7 | 92.7 |

TABLE 5

| Hours on stream | Equilibrium at 427° C. | 19–43 | 91–115 | 139–163 |
|---|---|---|---|---|
| Xylene Distribution % | | | | |
| Para- | 24.3 | 22.9 | 23.1 | 23.1 |
| Meta- | 52.4 | 54.2 | 55.5 | 55.5 |
| Ortho- | 23.3 | 22.9 | 21.4 | 21.4 |
| Approach to Equilibrium of each Xylene Isomer % | | | | |
| Para- | — | 85.6 | 86.7 | 86.7 |
| Meta- | — | 93.2 | 88.3 | 88.3 |
| Ortho- | — | 97.7 | 89.1 | 89.1 |

We claim:

1. A process for the hydrocatalytic treatment of a feedstock comprising a mixture of alkyl aromatics, containing at least one di- or polymethyl benzene and an alkyl benzene selected from ethyl-benzene, methylethylbenzene and propylbenzene which process comprises contacting said mixture at a temperature of from 300° to 500° C., a pressure of from 0 to 100 bars gauge and in the presence of hydrogen with a catalyst composition consisting essentially of an aluminosilicate having a gallium compound deposited thereon and/or an aluminosilicate in which the cations have been exchanged with gallium ions so that the monoalkylbenzenes mainly undergo isomerization to form xylenes or polymethyl benzenes, and recovering a product containing isomerised di- or polymethyl benzenes and a reduced content of the alkyl benzene.

2. A process according to claim 1 wherein the feedstock predominantly contains mixture of ethyl-benzene and isomeric xylenes.

3. A process according to claim 1 wherein the mole ratio of hydrogen in relation to the hydrocarbon at the time of contact with the catalyst is between 1:1 and 20:1.

4. A process according to claim 1 wherein the aluminosilicate used in the catalyst composition is a zeolite containing a molar ratio or silica to alumina of between 10:1 and 100:1.

5. A process according to claim 1 wherein the gallium in the catalyst composition is present as gallium oxide and/or as gallium ions when cations in the aluminosilicate support have been exchanged with gallium ions.

6. A process according to claim 5 wherein the aluminosilicates in which cations are exchanged with gallium ions are selected from mordenite, zeolite-$\beta$ and zeolites of the general formula $M_{2/n}O \cdot W_2O_3 \cdot ySiO_2 zH_2O$ wherein M is a cation which is a positively charged ion selected from a metal ion, an organic ion and a proton of valence n, W is either aluminium or a mixture thereof with gallium, y is an integer between 10 and 100 and z is from 0 to 40.

7. A process according to claim 6 wherein the cation M is represented by the formulae $R^1R^2R^3R^4N^+$ or by an ion derived from the diamine $R^1R^2N(CH_2)_xNR^3R^4$ or N-R'—pyrrolidine where $R^1R^2R^3$ and $R^4$ may be H, $CH_3$, $C_2H_5$, $C_3H_7$ or $C_4H_9$ and x equals 2, 3, 4, 5 or 6.

8. A process according to any of the preceding claims 5 wherein the zeolite is decationised prior to exchange with gallium ions.

9. A process according to claim 1 wherein the amount of gallium present in the catalyst composition is between 0.1 and 10% by weight of the total aluminosilicate in the catalyst.

10. A process according to claim 1 wherein the catalyst composition is activated prior to contact with the hydrocarbon feedstock at a temperature between 250° and 600° C. in an atmosphere of hydrogen air or a gas inert under the reaction conditions.

* * * * *

UNITED STATES PATENT AND TRADEMARK OFFICE
CERTIFICATE OF CORRECTION

PATENT NO. : 4,245,130
DATED : January 13, 1981
INVENTOR(S) : John R. Jones and Dennis C. Wood It is certified that error appears in the above-identified patent and that said Letters Patent are hereby corrected as shown below:

Col. 5, line 22, Example 2 - after "silica", delete "gel", and insert --sol-- in lieu thereof.

Signed and Sealed this

Twenty-eighth Day of July 1981

[SEAL]

Attest:

Attesting Officer

GERALD J. MOSSINGHOFF

Commissioner of Patents and Trademarks